United States Patent [19]

Altamura et al.

[11] Patent Number: 5,747,483

[45] Date of Patent: May 5, 1998

[54] PENEM DERIVATIVES, THEIR PREPARATION AND PHARMACEUTICAL COMPOSITIONS CONTAINING THEM

[75] Inventors: Maria Altamura, Florence; Federico Maria Arcamone, Nerviano; Enzo Perrotta, Florence; Vittorio Pestellini; Piero Sbraci, both of Florence; Giuseppe Cascio, Monza, all of Italy

[73] Assignees: A. Menarini Industrie Farmaceutiche Riunite, Florence; Istituto Lusofarmaco D'Italia, Milan, both of Italy

[21] Appl. No.: 414,081

[22] Filed: Mar. 17, 1995

Related U.S. Application Data

[63] Continuation of PCT/EP93/02493 filed on Sep. 15, 1993.

[51] Int. Cl.[6] .................. C07D 499/861; A61K 31/43
[52] U.S. Cl. ..................... 514/195; 540/310; 540/311; 514/192; 514/197
[58] Field of Search ........................ 540/310, 311; 514/195, 192, 197

[56] References Cited

FOREIGN PATENT DOCUMENTS

| 0 110 826 | 6/1984 | European Pat. Off. |
| 0 201 459 | 11/1986 | European Pat. Off. |
| 0 297 042 | 12/1988 | European Pat. Off. |
| 91 17955 | 11/1991 | WIPO |

OTHER PUBLICATIONS

Perrone et al., Chemical Abstracts, vol. 105, entry 60470 (1986).

C.S. Marvel et al., The Structure of Urea–Formaldehyde Resins, Sep. 17, 1946, Journal of the American Chemical Society, vol. 68, No. 9.

E. Fontana et al., Syntheses of [2-$^{14}$C] Penem Antibacterials; (FCE 22101 and FCE 22891), Journal of Labelled Compounds and Radiopharmaceuticals, vol. XXIV, No. 1, 1987.

A.J. Corraz, et al., Dual–Action Penems and Carbapenems, J. Med. Chem. 1992, 35, 1828–1839.

*Primary Examiner*—John M. Ford
*Attorney, Agent, or Firm*—Kenyon & Kenyon

[57] ABSTRACT

Penem derivatives of general formula (I), below, and pharmaceutically acceptable salts thereof are disclosed.

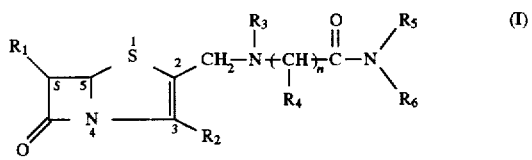

wherein: $R_1$ is H, $C_1$–$C_6$ alkoxy, $C_3$–$C_7$ cycloalkyl, or an optionally protected $C_1$–$C_6$ hydroxyalkyl; $R_2$ is a free or esterified carboxyl group or a carboxylate anion; $R_3$ is H or $C_1$–$C_6$ alkyl; $R_4$ is H, $C_1$–$C_6$ alkyl, $C_1$–$C_6$ hydroxyalkyl, $C_1$–$C_6$ mercaptoalkyl, $C_1$–$C_6$ aminoalkyl, $C_1$–$C_6$ alkyl substituted by a quaternary ammonium group, $C_1$–$C_6$ carboxyalkyl, cycloalkyl, aryl, arylalkyl, heterocyclyl-alkyl optionally substituted, saturated or unsaturated heterocycle, or $R_3$ and $R_4$ are linked together to form a heterocyclic ring having 3–7 atoms; $R_5$ and $R_6$ independently are H, $C_1$–$C_6$ alkyl, $C_1$–$C_6$ hydroxyalkyl, $C_1$–$C_6$ mercaptoalkyl, C–$C_6$ aminoalkyl, alkenyl, cycloalkyl, aryl, arylalkyl, alkylaryl, heterocyclyl-alkyl, $C_1$–$C_6$ alkyl carboxyamide, or $R_5$ and $R_6$ are taken together to form a heterocyclic ring having 3–7 atoms, and n is an intiger from 1 to 3.

8 Claims, No Drawings

PENEM DERIVATIVES, THEIR PREPARATION AND PHARMACEUTICAL COMPOSITIONS CONTAINING THEM

This application is a continuation-in-part of International Application PCT/EP93/02493 having an international filing date of Sep. 15, 1993.

Field of the Invention

The present invention refers to penem derivatives of general formula (I)

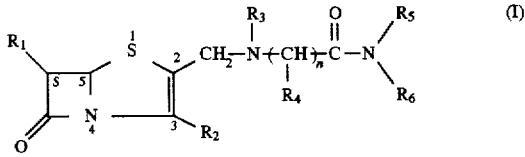

wherein:

$R_1$ is chosen in the group consisting of H, $C_1$–$C_6$ alkyl, $C_1$–$C_6$ alkoxy, $C_3$–$C_7$ cycloalkyl, optionally protected $C_1$–$C_6$ hydroxyalkyl $R_2$ is chosen in the group consisting of carboxyl group free or esterified with a group easily activated "in vivo", carboxylate anion $R_3$ is chosen in the group consisting of H, $C_1$–$C_4$ alkyl optionally substituted, $R_4$ is chosen in the group consisting of H, $C_1$–$C_6$ alkyl optionally substituted, $C_1$–$C_6$ hydroxyalkyl optionally substituted, $C_1$–$C_6$ mercaptoalkyl optionally substituted, $C_1$–$C_6$ aminoalkyl optionally substituted, $C_1$–$C_6$ alkyl substituted by a quaternary ammonium group, $C_1$–$C_6$ carboxyalkyl optionally substituted, $C_3$–$C_7$ cycloalkyl, $C_6$–$C_{10}$ aryl, $C_6$–$C_{10}$ aryl$C_1$–$C_6$alkyl, heterocyclyl-$C_1$–$C_6$alkyl optionally substituted, the side chain of a natural alpha-aminoacid, saturated or unsaturated $C_3$–$C_7$ heterocycle wherein the hetero-atoms in the heterocyclic ring can be N, O, S or $R_3$ and $R_4$ linked together form an heterocyclic ring having 3–7 atoms, optionally substituted, saturated or unsaturated which can contain other hetero-atoms as O, N, S.

$R_5$ and $R_6$ independently from one another are chosen in the group consisting of H, $C_1$–$C_6$ alkyl, $C_1$–$C_6$ hydroxyalkyl, $C_1$–$C_6$ mercaptoalkyl, $C_1$–$C_6$ aminoalkyl, $C_2$–$C_6$ alkenyl, $C_3$–$C_7$ cycloalkyl, $C_6$–$C_{10}$ aryl, $C_6$–$C_{10}$aryl$C_1$–$C_6$alkyl, $C_1$–$C_6$alkyl$C_6$–$C_{10}$aryl, heterocyclyl-$C_1$–$C_6$alkyl, $C_1$–$C_6$ alkyl carboxyamide wherein the alkyl group can be linear or branched (all these group optionally substituted)

or $R_5$ and $R_6$ taken together form an heterocyclic ring having 3–7 atoms optionally substituted n is chosen in the group consisting of: 1, 2, 3 and their pharmaceutically acceptable salts.

State of the Art

The compounds known as penems represent a wide family of compounds having antibacterial properties.

Since bacteria become rapidly resistant to agents used against them it is important to develop new compounds in order to satisfy the pharmacological request of medicaments being effective against infective agents (known or not yet known), having good stability, less toxicity etc.

Description of the Invention

The present invention makes available new compounds of the penem family having interesting pharmaceutical properties.

The compounds according to the present invention are compounds of formula (I)

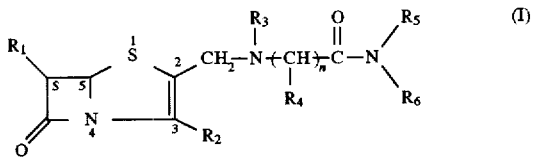

wherein $R_1$, $R_2$, $R_3$, $R_4$, $R_5$, $R_6$ and n are as above defined.

It is evident from the above formula (I) that the compounds according to the invention may consist of various optical and geometrical isomers, such isomers, as well as their mixtures, are obviously considered to be included in the scope of the present invention.

Preferred are those compounds of formula (I) having the configuration (5R, 6S).

Preferred are the compounds of formula (I) wherein $R_1$=alphahydroxy ethyl and more particularly those in which such group has the configuration 1R i.e. the configuration of the alpha-C atom of the ethyl group is R.

$R_2$ is carboxylate anion or a carboxylic group free or esterified with a group easily activable "in vivo" chosen in the group consisting of the compunds of general formula (a) and (b)

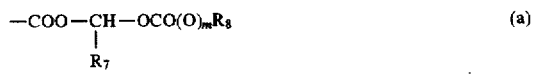

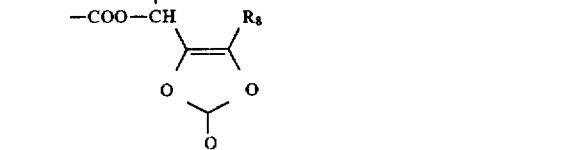

wherein $R_7$ and $R_8$ are chosen in the group consisting of: H, $C_1$–$C_6$ alkyl, $C_2$–$C_6$ alkenyl, $C_3$–$C_8$ cycloalkyl or cycloalkenyl, $C_6$–$C_{10}$ aryl or $C_1$–$C_6$alkyl$C_6$–$C_{10}$aryl and m is 0 or 1.

Among the groups easily activable "in vivo" are for example:

-acetoxymethyl [(a): $R_7$=H; $R_8$=$CH_3$; m=0]
-propanoyloxymethyl [(a): $R_7$=H; $R_8$=$CH_2CH_3$; m=0]
-pivaloyloxymethyl [(a): $R_7$=H; $R_8$=$C(CH_3)_3$; m=0]
-1-acetoxyethyl [(a): $R_7$=$CH_3$; $R_8$=$CH_3$; m=0]
-1-acetoxypropyl [(a): $R_7$=$CH_2CH_3$; $R_8$=$CH_3$; m=0]
-1-cyclohexylcarbonyloxyethyl [(a): $R_7$=$CH_3$; $R_8$=cyclohexyl; m=0]
-benzoyloxymethyl [(a): $R_7$=H; $R_8$=Ph; m=0]
-1-benzoyloxyethyl [(a): $R_7$=$CH_3$; $R_8$=Ph; m=0]
-methoxycarbonyloxymethyl [(a): $R_7$=H; $R_8$=$CH_3$; m=1]
-1-methoxycarbonyloxyethyl [(a): $R_7$=$CH_3$; $R_8$=$CH_3$; m=1]
-isopropyloxycarbonyloxymethyl [(a): $R_7$=H; $R_8$=$CH(CH_3)_2$; m=1]
-1-isopropyloxycarbonyloxyethyl [(a): $R_7$=$CH_3$; $R_8$=$CH(CH_3)_2$; m=1]
-ciclohexyloxycarbonyloxymethyl [(a): $R_7$=H; $R_8$=cyclohexyl; m=1]
-cyclohexylmethyloxycarbonyloxymethyl [(a): $R_7$=H; $R_8$=cyclohex-$CH_2$; m=1]
-1-cyclohexyloxycarbonyloxyethyl [(a): $R_7$=$CH_3$; $R_8$=cyclohexyl; m=1]
-(2-oxo-1,3-dioxolen-4-yl)methyl [(b): $R_7$=H; $R_8$=H]
-(5-methyl-2-oxo-1,3-dioxolen-4-yl)methyl [(b): $R_7$=H; $R_8$=$CH_3$]-(5-tert-butyl-2-oxo-1,3-dioxolen-4-yl)methyl [(b): $R_7$=H; $R_8$=$C(CH_3)_3$]

-(5-phenyl-2-oxo-1,3-dioxolen-4-yl)methyl |(b): R₇=H; R₈=Ph]

R₃ is preferably a methyl or ethyl group optionally substituted.

R₄ is preferably H, $C_1$-$C_6$ alkyl optionally substituted, $C_1$-$C_6$ hydroxyalkyl, $C_1$-$C_6$ mercaptoalkyl, $C_1$-$C_6$ aminoalkyl, $C_1$-$C_6$ carboxyalkyl, aryl optionally substituted, arylalkyl, for example benzyl, alkyl $C_1$-$C_6$ substituted by a quaternary ammonium-group, heterocyclyl-$C_1$-$C_6$alkyl or the side chain of a natural alpha-aminoacid. When R₃ and R₄ are joined together they form a ring having 3-7 atoms, optionally substituted, wherein other heteroatoms than N can be present for example 1-pyrrolidine, 1-azetidine, 1-piperidine, 4-morpholine, 1-piperazine, 4-methyl-piperazine.

R₅ and R₆ are preferably H, $C_1$-$C_6$ alkyl, $C_6$-$C_{10}$ aryl, $C_6$-$C_{10}$aryl$C_1$-$C_6$ alkyl, $C_1$-$C_6$alkyl$C_6$-$C_{10}$aryl, $C_1$-$C_6$alkylcarboxyamide, or together they form an heterocyclic ring having 3-7 atoms optionally substituted, as for example : 1-aziridine, 1-azetidine, 1-pyrrolidine, 1-piperidine, 4-morpholine, 1-piperazine, 4-metylpiperazine.

Among the possible substituent groups are preferred : methyl, ethyl, propyl, butyl, pentyl, cyclopentyl, cyclohexyl, phenyl, benzyl, OH, $C_1$-$C_6$alkoxy, carboxyamidic group (optionally substituted), carboxyester, carbamoyloxy.

Among the pharmacological acceptable salts of the compounds of formula (I) according to the present invention are those commonly used in the field of penicillin and cephalosporin as for example the salts formed with inorganic bases as alkali metal hydroxide or earth alkaline metal hydroxyde (preferably NaOH, KOH) and salts of organic bases included aminoacids as for example lysine; pharmacological acceptable salts according to the invention include also internal salts (zwitterions).

Compounds of formula (I) according to the invention are for example:

(5R,6S)-2-(N-(2-acetamido)-N-methyl)-aminomethyl)-6-[(1R)-1-hydroxyethyl]-penem-3-carboxylic acid (5R,6S)-2-((N-prolinamido)-methyl)-6-[(1R)-1-hydroxyethyl]-penem-3-carboxylic acid (5R,6S)-2-(N-methyl-phenylalaninamido)-methyl-6-[(1R)-1-hydroxyethyl]-penem-3-carboxylic acid (5R,6S)-2-(3'-carboxyamido-piperidin-1'-yl)-methyl-6-[(1R)-1-hydroxyethyl]-penem-3-carboxylic acid (5R,6S)-2-(N,N-diacetamido)-aminomethyl-6-[(1R)-1-hydroxy-ethyl]-penem-3-carboxylic acid (5R,6S)-2-(N-methyl-N-(3'-propionamido)-aminomethyl-6-[(1R)-1-hydroxyethyl]penem-3-carboxylic acid (5R,6S)-2-(N-methyl-N-(4'-methyl-1'piperazin)amidocarboxy-methyl-aminomethyl-6-[(1R)-1-hydroxyethyl]-penem-3-carboxylic acid (5R,6S)-2-(N-ethyl-N-(2'-acetamido)-aminomethyl-6-[(1R)-1-hydroxyethyl]-penem-3-carboxylic acid (5R,6S)-2-(N-methyl-N-((N',N'-dimethyl)acetamido)-amino-methyl-6-[(1R)-1-hydroxyethyl]-penem-3-carboxylic acid (5R,6S)-2-(2'-carboxyamido-piperidin-1'-yl)-methyl-6-[(1R)-1-hydroxyethyl]-penem-3-carboxylic acid (5R,6S)-2-(4'-carboxyamido-piperidin-1'-yl)-methyl-6-[(1R)-1-hydroxyethyl]-penem-3-carboxylic acid (5'-Methyl-2'-oxo-1',3'-dioxolen-4'-yl)methyl(5R,6S)-2-(N-prolinamido)methyl-6-[(1R)-1-hydroxyethyl]-penem-3-carboxylate Acetoxymethyl (5R,6S)-2-[(N-methyl-N-(2-acetamido))-amino-methyl-6-[(1R)-1-hydroxyethyl]-penem-3-carboxylate (5R,6S)-2-(2'-carboxyamido-aziridin-1'-yl)-methyl-6-[(1R)-1-hydroxyethyl]-penem-3-carboxylic acid (5R, 6S) -2- (N-(D-prolinamido)) -methyl-6-[(1R)-1-hydroxy-ethyl]-penem-3-carboxylic acid (5R,6S)-2-|N-methyl-(N'-glycinamido)-glycyl|-aminomethyl-6-|(1R)-1-hydroxyethyl|-penem-3-carboxylic acid Sodium (5R,6S)-2-(N-methyl-N-(2-acetamido)-aminomethyl-6-[(1R)-1-hydroxyethyl]-penem-3-carboxylate Acetoxymethyl (5R,6S)-2-(N-prolinamido)methyl-6-[(1R)-1-hydroxyethyl]-penem-3-carboxylate (5'-methyl-2'-oxo-1',3'-dioxolen-4'-yl)methyl (5R,6S)-2-(N-(2-acetamido)-N-methyl]-aminomethyl-6-[(1R)-1-hydroxyethyl]-penem-3-carboxylate (5R,6S)-2-|(2'S,4'R)-2'-carboxyamido-4'-hydroxy-pyrrolidin-1'-yl]-methyl-6-[(1R)-1-hydroxyethyl]-penem-3-carboxylic acid (5R,6S)-2-(N-(2S)-2-propionamido-N-methyl]-aminomethyl-6-[(1R)-1-hydroxyethyl]-penem-3-carboxylic acid Pivaloyloxymethyl (5R,6S)-2-(N-prolinamido)methyl-6-[(1R)-1-hydroxyethyl]-penem-3-carboxylate Pivaloyloxymethyl (5R,6S)-2-(N-acetamido)-N-methyl-6-[(1R)-1-hydroxyethyl]-penem-3-pivaloyloxymethyl carboxylate.

The products of the present invention can be administered as such other in combination with the excipients commonly used with penicillins and cephalosporins for the preparation of formulations for the oral or parenteral use or in combination with known antibiotics or with inhibitors of beta-lactamases.

The compounds according to the present invention have a widespread antibacterial activity and can be administered in the doses and according to the modality already known in pharmacopeia for the analogous penicillins and analogous antibiotics.

The compounds according to the present invention can be prepared from the corresponding hydroxymethyl compounds of formula II (SCHEME 1) wherein R₁ is as defined (preferably alpha-hydroxyethyl) and Y is an ester-group as for example allyl or p-nitrobenzyl.

The compounds of formula II are known and can be prepared (SCHEME 1) from the azetidinone compounds III or from the derivatives of natural penicillins IV using known procedures [for example E. Fontana et al., J.Lab.Comp.Radiopharm., 24, 41 (1986); A. J.Corraz et al., J.Med.Chem.,35, 1828 (1992) here reported for reference].

SCHEME 1

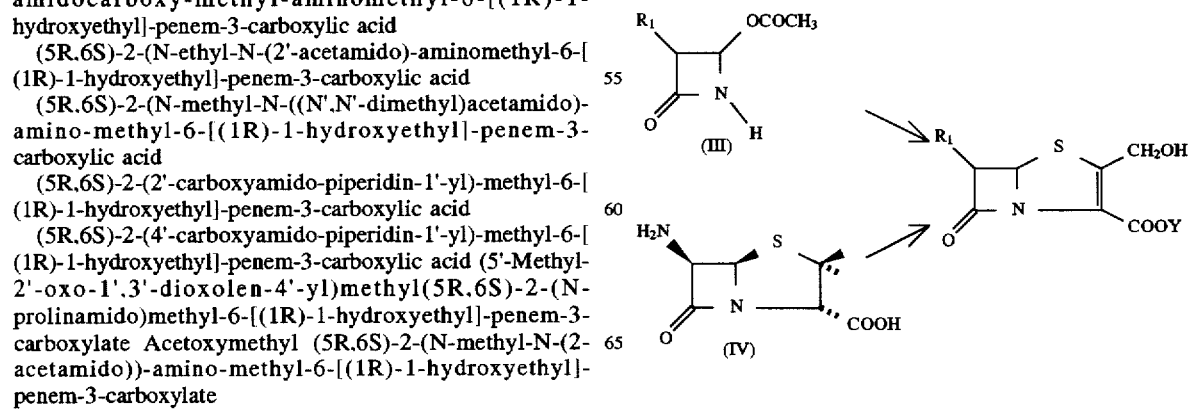

-continued
SCHEME 1

(II) ⟶

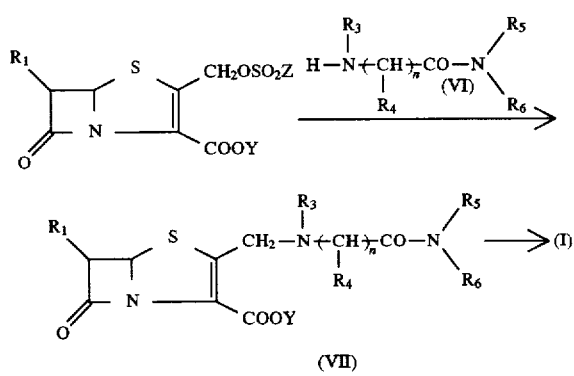

(VII)

The hydroxymethyl penems II are transformed into the corresponding sulfonyl derivatives V, wherein $R_1$ and Y are as above defined and Z is an alkyl- or aryl-group (preferably methyl or p-tolyl), by reacting compounds II with the appropriate sulfonyl chloride in the presence of an organic base, as for example triethylamine or N,N-diisopropylethylamine, in an inert organic solvent, as for example dichloromethane or chloroform, at a temperature ranging from $-70°$ C. and $+20°$ C. The sulfonyl derivatives V are reacted with the compounds of formula VI, where n, $R_3$, $R_4$, $R_5$ and $R_6$ are as above defined, in an organic solvent as for example dimethylsulfoxide, dimethylformamide, dioxane, tetrahydrofuran or ethyl acetate at a temperature of $-20°$ C. $-+20°$ C.; the reaction can be performed on the derivatives V crude or pure. Alternatively the synthesis can be performed by transforming the sulfonyl derivatives V into the corresponding halides VIII

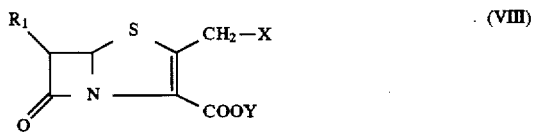

Wherein X is chlorine, bromine or iodine through a reaction with inorganic halides preferably calcium halides.

The compounds of general formula VII can be obtained from the halides VIII through a reaction with the compounds of formula VI wherein n, $R_3$, $R_4$, $R_5$ and $R_6$ are as above defined in an organic solvent as for example dimethylsulfoxide, dimethylformamide, dioxane, tetrahydrofuran or ethylacetate at a temperature of $-20°$ C. $-+20°$ C.; also in this case the reaction can be perfomed starting from the corresponding halides VIII isolated or crude. At the end of the reaction the penems VII are isolated and characterised with conventional methods.

When $R_1$ is an hydroxyalkyl group the reaction sequence is performed after protecting the alcoholic function with the conventional protecting groups as for example p-nitrobenzyloxycarbonyl, allyloxycarbonil, t-butyldimethylsilyl or trimethylsilyl. The protecting group is removed at the end of the reactions sequence. Alternatively, the reaction can be performed with the dialcoholic derivative II not protected ($R_1$=$CH_3$CHOH—).

The compounds of general formula I are finally obtained from the corresponding esters VII through hydrolysis or hydrogenolysis or with other procedures.

The compounds of general formula I possess a remarkable antibacterial activity when compared with the conventional beta-lactam antibiotics, both against gram-positive and gram-negative microorganisms and also against anaerobic microorganisms either producing or not-producing beta-lactamases.

EXAMPLE 1

Allyl (5R,6S)-2-(N-(2-acetamido)-N-methyl)-aminomethyl) -6-[(1R) -1-ter-butyldimethylsilyloxyethyl]-penem-3-carboxylate 3.2 ml (23.2 mmoles) of triethylamine and 1.8 ml (23.2 mmoles) of methanesulfonyl chloride are added at 0° C. under nitrogen atmosphere to a solution of 6 g (15 mmoles) of allyl (5R,6S)-2-hydroxymethyl-6-[(1R)-1-ter-butyldimethyl-silyloxy-ethyl]-penem-3-carboxylate in 150 ml of anhydrous methylene dichloride. The reaction mixture is stirred at 5° C. for 30 minutes. The cold solution is washed with water, NaHCO$_3$ 5% and again with water. The solution is dried over Na$_2$SO$_4$ and is evaporated giving a yellow residue.

The crude product is dissolved in dimethylsulfoxide (150 ml) and a solution of 2.4 g (19.3 mmoles) of sarcosinamide hydrochloride [prepared according to Marvel et al. J.Am.Chem.Soc., 68, 1685 (1946)] and 2.8 ml (20.1 mmoles) of triethylamine in 40 ml of dimethylsulfoxide is added. 2.8 ml (20.1 mmoles) of triethylamine are added to the solution and the mixture is stirred at room temperature for 4 hours. The mixture is left for 1 night at the same temperature and is poured into water and ice and extracted twice with ethyl acetate. The organic extracts are washed with water and dried over Na$_2$SO$_4$ and the solvent is evaporated under vacuum. The crude product is purified by column-chromatography (silica gel; ethyl acetate/ cyclohexane 70:30 v/v), giving a pale yellow solid; m.p.: 118–9° C.

EXAMPLE 2

Allyl (5R,6S)-2-(N-(2-acetamido)-N-methyl)-aminomethyl) -6-[(1R)-1-hydroxyethyl]-penem-3-carboxylate Acetic acid 2.9 ml (50.7 mmoles) and tetrabutylammonium fluoride (1M solution in tetrahydrofuran; 25 ml, 25 mmoles) are added at room temperature to a solution of allyl (5R,6S)-2-(N-(2-acetamido)-N-methyl)-aminomethyl)-6-[ (1R)-1-ter t-butyl-dimethylsilyloxyethyl]-penem-3-carboxylate (4 g; 8.5 mmoles) in tetrahydrofuran (200 ml). The mixture is stirred for 24 hours at room temperature, is concentrated at 50 ml, diluted with ethyl acetate, washed with water and NaHCO$_3$ 5%, dried and evaporated.

The residue is crystallized from ethyl ether, washed on the filter with ethyl ether and dried under vacuum giving a yellow solid; m.p.: 83–85° C.

EXAMPLE 3

(5R,6S)-2-(N-(2-acetamido)-N-methyl)-aminomethyl)-6-[ (1R)-1-hydroxyethyl]-penem-3-carboxylic acid 80 mg (0.30 mmoles) triphenylphosphine, 335 mg (0.29 mmoles) tetrakis(triphenylphosphine)palldium(0) and 0.24 ml (4.2 mmoles) acetic acid are added at 35°–40° C. under nitrogen atmosphere to a solution of 1 g (2.8 mmoles) of allyl (5R,6S)-2-(N-(2-acetamido)-N-methyl)-aminomethyl) -6-[(1R)-1-hydroxyethyl]-penem-3-carboxylate in 60 ml of anhydrous tetrahydrofuran and 60 ml of anhydrous methylene dichloride.

The mixture is stirred at the same temperature for about one hour. The solution is concentrated to 50 ml and is added with ethyl ether under stirring; the precipitate is filtered under nitrogen atmosphere, washed with ethyl ether and dried under vacuum. The crude product is purified by reverse phase column chromatography (LiChroprep RP-18[R]; water/acetone 95:5 v/v).

EXAMPLE 4
Allyl (5R,6S)-2-((N-prolinamido)methyl)-6-[(1R)-1-ter-butyl-di-methylsilyloxyethyl]-penem-3-carboxylate 1.0 ml (7.2 mmoles) of triethylanmine and 0.6 ml (7.7 mmoles) of methanesulfonyl chloride are added at 0° C. under nitrogen atmosphere, to a solution of 2 g (5 mmoles) of allyl (5R,6S)-2-hydroxymethyl-6-[(1R)-1-ter-butyldimethylsilyloxy-ethyl]-penem-3-carboxylate in 60 ml of anhydrous methylene dichloride.

The mixture is stirred for 30 minutes at 5° C. and thereafter is washed with water, NAHCO$_3$ 5% and again with water. The solution is dried over Na$_2$SO$_4$ and evaporated giving a yellow residue.

The crude product is dissolved in dimethylsulfoxide (60 ml). 0.7 g (6 mmoles) of prolinamide and 0.7 ml (5 mmoles) of triethylamine are added to the solution which is stirred at room temperature for 2 hours and is therefater left at room temperature for a night. The solution is poured into water and ice and is extracted twice with ethyl acetate. The organic extracts are collected together, washed with water, dried over Na$_2$SO$_4$ and evaporated under vacuum.

The crude product is purified by column chromatography (silica gel; ethyl acetate) giving a pale yellow wax.

EXAMPLE 5
Allyl (5R,6S)-2-((N-prolineamido)-methyl)-6-[(1R)-1-hydroxy-ethyl]-penem-3-carboxylate 0.9 ml (15.7 mmoles) of acetic acid and 2.5 g (7.9 mmoles) of tetrabutylammonium fluoride trihydrate are added, at room temperature, to a solution of allyl (5R,6S)-2-((N-prolin-amido)-methyl)-6-[(1R)-1-tert-butyldimethylsilyloxyethyl]-penem-3-carboxylate (1.3 g; 2.62 mmoles) in tetrahydrofuran (70 ml). The mixture is stirred at room temperature for 16 hours, is diluted with ethyl acetate, washed with water and NaHCO$_3$ 5%, dried and evaporated. The compound is purified through column chromatography (silica gel; ethyl acetate).

Yellow oil.

EXAMPLE 6
(5R, 6S) -2- ( (N-prolinamido) -methyl) -6-[(1R)-1-hydroxyethyl]-penem-3-carboxylic acid 130 mg (0.50 mmoles) of triphenylphosphine, 560 mg (0.48 mmoles) of tetrakis(triphenylphosphine)palladium(0) and acetic acid (0.27 ml; 4.7 mmoles) are added, at room temperature under nitrogen atmosphere, to a solution of (5R,6S)-2-((N-prolinamido)-methyl)-6-[(1R)-1-hydroxyethyl]-penem-3-allyl carboxylate (0.93 g; 2.4 mmoles) in 100 ml of anhydrous tetrahydrofuran.

The mixture is stirred at the same temperature for 30 minutes, thereafter is diluted with ethyl ether, the precipitate is filtered under nitrogen, washed with ethyl ether and dried under vacuum. The crude product is purified by reverse phase column chromatography (LiChroprep RP-18$_R$; water/acetone 95:5 v/v)

White solid, m.p.: 133–5° C.; M.W.: 341.38

EXAMPLE 7
(5'-Methyl-2'-oxo-1',3'-dioxolen-4'yl)-methyl (5R,6S)-2-(N-(2-acetamido)-N-methyl)aminomethyl)-6-[(1R)-1-hydroxyethyl]-penem-3-carboxylate 106 mg (1.0 mmoles) of anhydrous sodium carbonate are added, at room temperature and under nitrogen atmosphere to a solution of 261 mg (0.83 mmoles) of (5R,6S)-2-(N-(2-acetamido)-N-methyl)aminomethyl)-6-[(1R)-1-hydroxyethyl]-penem-3-carbo-xylic acid in dimethylformamide (15 ml).

The mixture is stirred for 3 hours at room temperature, is cooled to 0° C. and is added with 192 mg (1.0 mmoles) of 4-bromomethyl-5-methyl-1,3-dioxolen-2-one) which is reacted for 2 hours at room temperature. The solution is diluted with ethyl acetate, washed with water, dried over Na$_2$SO$_4$ and evaporated.

The residue is precipitated from chloroform/cyclohexane, solubilised with water and lyophilised.

The product is purified by HPLC using a column Hypersil 10 ODS$^R$, 10 um, 25 cm×20 mm, mobile phase: water/acetonitrile 40/60, flow 10 ml/min. Obtained 105 mg (Yield 30%). M. W: 427.43.

HPLC (analytical): column : Hypersil 5 ODS$^R$, 5 um, 25 cm×4.6 mm, UV detector: 220 and 320 nm, mobile phase: water/acetonitrile (40/60), flow: 1 ml/min, t$_R$=5.8 min, lambda$_{max}$=325 nm.

EXAMPLE 8
Sodium (5R,6S)-2-(N-(2-acetamido)-N-methyl) aminomethyl-6-[(1R)-1-hydroxyethyl]-penem-3-carboxylate 35 mg (0.13 mmoles) of triphenylphosphine, 145 mg (0.12 mmoles) of tetrakis(triphenylphosphine)palladium(0) and 326 mg (1.96 mmoles) of sodium 2-ethylhexanoate are added, at room temperature, under nitrogen atmosphere, to a solution of 450 mg (1.26 mmoles) of allyl (5R,6S)-2-(N-(2-acetamido)-N-methyl)aminomethyl)-6-[(1R)-1-hydroxyethyl]-penem-3-carboxylate in 10 ml of anhydrous tetrahydrofuran. The mixture is stirred at room temperature for 30 minutes.

The solution is concentrated giving a raw product which is purified through HPLC using a column Hypersil 10 ODS$^R$, 10 um, 25 cm×20 mm; mobile phase: water/acetonitrile: 90/10, flow: 20 ml/min. Obtained: 235 mg (Yield 54%). M.W.: 338.34.

HPLC (analytical), column: Hypersil 5 ODS$^R$, 5 um, 25 cm×4.6 mm, UV detector: 220 and 320 nm, mobile phase: water/acetonitrile (95/5), flow: 1 ml/min, t$_R$ 4.0 min.

Following the procedure described in the examples 3, 6, 7 and 8 and using the appropriate reagents the following compounds were also obtained:

(5R,6S)-2-(N-methyl-phenylalaninamido)-methyl-6-[(1R)-1-hydroxyethyl]-penem-3-carboxylic acid
M.W.=405.47
MS(FAB):m/z 406 (M+H$^+$)
HPLC, phase: water/acetonitrile (80/20); t$_R$=5.7 min (5R,6S)-2-(3'-carboxyamido-piperidin-1'-yl)-methyl-6-[(1R)-1-hydroxyethyl]-penem-3-carboxylic acid
M.W.=355.412

[Two diastereoisomers were obtained (A) and (B); these were separated by HPLC (preparative), phase: water/acetonitrile (95/5); column Hypersil 10 ODS$^R$, 10 um, 25 cm×20 mm, flow 20 ml/min]HPLC (analytical): t$_R$(A)=8.2; t$_R$(B)=9.9 min (5R,6S)-2-(N,N-diacetamido)-aminomethyl-6-[(1R)-1-hydroxy-ethyl]-penem-3-carboxylic acid
M.W.: 358.37
MS(FAB):m/z 359 (M+H$^+$) $^{13}$C NMR (50 MHz, D$_2$0)Δ (ppm) characterising signals: 56.0, 61.1, 66.8, 69.1, 74.0

(5R,6S)-2-(N-methyl-N-(3'-propionamido)-aminomethyl-6-[(1R)-1-hydroxyethyl]penem-3-carboxylic acid M.W.=329.37
HPLC: t$_R$=5.0 min, lambda$_{max}$=314 nm (5R,6S)-2-(N-methyl-N-(4'-methyl-1'piperazin) amidocarboxy-methyl-aminomethyl-6-[(1R)-1-hydroxyethyl]-penem-3-carboxylic acid
M.W.: 398.48
$^{13}$C NMR (50 MHz, D$_2$0) Δ (ppm) characterising signals : 46.3, 47.4, 59.9, 67.9, 69.0, 74.6

---

White solid; m.p.: 92–95° C.; M.W. : 315.35

(5R,6S)-2-(N-ethyl-N-(2'-acetamido)-aminomethyl-6-[(1R)-1-hydroxyethyl]-penem-3-carboxylic acid
M.W.: 329.37
HPLC: $t_R$=4.8 min; lambda$_{max}$=310 nm (5R,6S)-2-(N-methyl-N-((N',N'-dimethyl)acetamido)-amino-methyl-6-[(1R)-1-hydroxyethyl]-penem-3-carboxylic acid
M.W.: 343.40
HPLC: $t_R$=9.1 min, lambda$_{max}$=315 nm (5R,6S)-2-(2'-carboxyamido-piperidin-1'-yl)-methyl-6-[(1R)-1-hydroxyethyl]-penem-3-carboxylic acid
M.W.:355.411

[Two diastereoisomers were obtained (A) and (B); these were separated by HPLC (preparative), phase: water/acetonitrile (99/1); column Hypersil 10 ODS$^R$, 10 um, 25 cm×20 mm, flow 20 ml/min]
HPLC (analytical): $t_{R(A)}$=9.1; $t_{R(B)}$=11.0 min (5R,6S)-2-(4'-carboxyamido-piperidin-1'-yl)-methyl-6-[(1R)-1-hydroxyethyl]-penem-3-carboxylic acid
M.W.: 355.412
m. p.: 136°–7° C.

(5'-Methyl-2'oxo-1',3'-dioxolen-4'-yl)methyl(5R,6S)-2-(N-prolinamido)methyl-6-[(1R)-1-hydroxyethyl]-penem-3-carboxylate
M.W.: 453.470
MS(EI): m/z 453 (M$^+$)
HPLC: phase water/acetonitrile (20/80), $t_R$=4.2 min; lambda$_{max}$=325 nm Acetoxymethyl (5R,6S)-2-(N-methyl-N-(2-acetamido))-amino-methyl-6-[(1R)-1-hydroxyethyl]-penem-3-carboxylate
M.W.: 387.41
HPLC:phase water/acetonitrile (50/50), $t_R$=3.0 min
MS(TS): m/z 388 (M+H$^+$)

(5R,6S)-2-(2'-carboxyamido-aziridin-1'-yl)-methyl-$^6$-[(1R)-1-hydroxyethyl]-penem-3-carboxylic acid
M.W.: 313.33
HPLC: phase water/acetonitrile (98/2), $t_R$=1.8 min; lambda$_{max}$=306 nm
MS(FAB): m/z 314 (M+H$^+$)

(5R,6S)-2-(N-(D-prolinamido))-methyl-6-[(1R)-1-hydroxy-ethyl]-penem-3-carboxylic acid
M.W.: 341.38
HPLC: phase water/acetonitrile (95/5), $t_R$=4.4 min
MS(FAB): m/z 342 (M+H$^+$)

(5R,6S)-2-[N-methyl-(N'-glycinamido)-glycyl]-aminomethyl-6-[(1R)-1-hydroxyethyl]-penem-3-carboxylic acid
M.W.: 372.40
HPLC: phase water/acetonitrile (95/5), $t_R$=3.4 min; lambda$_{max}$=308 nm
MS(FAB): m/z 373 (M+H$^+$)

Acetoxymethyl (5R,6S)-2-(N-prolinamido)methyl-6-[(1R)-1-hydroxyethyl]-penem-3-carboxylate
M.W.: 413.449
HPLC: phase water/acetonitrile (50/50); $t_R$=11.1 min; lambda$_{max}$=328 nm.
MS(TS): m/z 414 (M+H$^+$)

(5R,6S)-2-[(2'S,4'R)-2'-carboxyamido-4'-hydroxypyrrolidin-1'-yl]-methyl-6-[(1R)-1-hydroxyethyl]-penem-3-carboxylic acid
M.W.: 357.38
HPLC: phase: water (100%), $t_R$=3.0 min; lambda$_{max}$=306 nm
MS(FAB): m/z 358 (M+H$^+$)

(5R,6S)-2-(N-(2S)-2-propionamido-N-methyl]-aminomethyl-$^6$-[(1R)-1-hydroxyethyl]-penem-3-carboxylic acid
M.W.: 329.1
M.p.: 105° C. (dec.)

Pivaloyloxymethyl (5R,6S)-2-(N-prolinamido)methyl-6-[(1R)-1-hydroxyethyl]-penem-3-carboxylate
M.W.: 455.17
M.p.: 51°–5° C.

Pivaloyloxymethyl (5R,6S)-2-(N-acetoamido)-N-methyl-6-[(1R)-1-hydroxyethyl]-penem-3-carboxylate
M.W.: 429.16
M.p.: 50°–3° C.

The operative conditions of the HPLC (analytical) are the following (when not differently reported):

column Hypersil 50DS$^R$, 5um, 25 cm×4.6 mm, UV detector 220 and 320 nm, phase water/acetonitrile (95/5), flow 1 ml/min.

(5R,6S)-2-[N-(2'R)-2'-propionamido-N-methyl]aminomethyl-6-[(1R)-1-hydroxyethyl]-penem-3-carboxylic acid
m.p. 145° C.
HPLC: column: µBondalPack C$_{18}$; phase: water/acetonitrile 95:5.

(5R, 6S) -2-[(2'R, 4'R) -2'-carboxyamido-4'-hydroxypyrrolidin-1'-yl]methyl-6-[(1R)-1-hydroxyethyl]-penem-3-carboxylic acid
m. p. 118°–123° C.

(5R,6S)-2-[(2'S,4'S)-2'-carboxyamido-4'-hydroxypyrrolidin-1'-yl]methyl-6-[(1R)-1-hydroxyethyl]-penem-3-carboxylic acid
m. p. 98°–103° C.

(5R, 6S) -2- [(2'R, 4'S) -2'-carboxyamido-4'-hydroxypyrrolidin-1'-yl]methyl-6-[(1R)-1-hydroxyethyl]-penem-3-carboxylic acid (5R,6S)-2-[(2'S,4'R)-2'-carboxyamido-4'-carbamoyloxypyrrolidin-1'-yl]methyl-6-[(1R)-1-hydroxyethyl]-penem-3-carboxylic acid
m. p. 122°–25° C.

(5R,6S)-2-[(2'S,4'R)-2'-carboxyamido-4'-acetyloxypyrrolidin-1'-yl]methyl-6-[(1R)-1-hydroxyethyl]-penem-3-carboxylic acid
m. p. 85°–88° C.

(5R,6S)-2-[(2'S,4'S)-2'-carboxyamido-4'-aminopyrrolidin-1'-yl]methyl-6-[(1R)-1-hydroxyethyl]-penem-3-carboxylic acid
m. p. 162°–8° C.

Acetoxymethyl (5R,6S)-2-[N-(D-prolinamido)]methyl-6-[(1R)-1-hydroxyethyl]-penem-3-carboxylate
m. p. 135°–40° C. HPLC: column: µBondalPack C$_{18}$; phase: water/acetonitrile 50:50. Pivaloyloxymethyl (5R,6S) -2-[N-(D-prolinamido)]methyl-6-[(1R)-1-hydroxyethyl]-penem-3-carboxylate
m. p. 130°–35° C.

HPLC: column: µBondaPack C$_{18}$; phase: water/acetonitrile 50:50. (5-methyl-2-oxo-1,3-dioxol-4-yl) methyl (5R,6S)-2-[N-(D-prolinamido)]methyl-6-[(1R)-1-hydroxyethyl]-penem-3-carboxylate
m. p. 165°–70° C.

HPLC:column: µBondaPack C$_{18}$; phase: water/acetonitrile 50:50. Acetoxymethyl (5R,6S)-2-[N-(2'S)-2'-propionamido-N-methyl]aminomethyl-$^6$-[(1R)-1-hydroxyethyl]-penem-3-carboxylate
m. p. 138°–42° C.

HPLC: column: µBondapack C$_{18}$; phase: water/acetonitrile 50:50. Pivaloyloxymethyl (5R,6S)-2-[N-(2'S)-2'-propionamidol-N-methyl]-aminomethyl-6-[(1R)-1-hydroxyethyl]-penem-3-carboxylate
m. p. 151°–53° C.

HPLC: column: µBondaPack C$_{18}$; phase: water/acetonitrile 50:50. (5-methyl-2-oxo-1,3-dioxol-4-yl)methyl (5R,6S)-2-[N-(2'S)-2'-propionamido-N-methyl] aminomethyl-6-[(1R)-1-hydroxyethyl]-penem-3-carboxylate m. p. 153°–55° C.

HPLC: column: μBondaPack $C_{18}$; phase: water/ acetonitrile 50:50. Pivaloyloxymethyl (5R,6S)-2-[(2'S,4'R)-2'-carboxyamido-4'-hydroxy-pyrrolidin-1'-yl]methyl-6-[(1R)-1-hydroxyethyl]-penem-3-carboxylate m. p. 158°–60° C.

HPLC: column: μBondaPack $C_{18}$; phase: water/ acetonitrile 50:50. (5-methyl-2-oxo-1,3-dioxol-4-yl)methyl (5R,6S)-2-[(2'S,4'R)-2-carboxyamido-4'-hydroxy-pyrrolidin-1'-yl]methyl-6-[(1R)-1- hydroxyethyl]-penem-3-carboxylate m. p. 160°–62° C.

HPLC: column: μBondaPack $C_{18}$; phase: water/ acetonitrile 50:50. Cyclohexylcarbonyloxymethyl (5R,6S)-2-[(2'S,4'R)-2'-carboxyamido-4''-hydroxy-pyrrolidin-1'-yl]methyl-6-[(1R)-1-hydroxyethyl]-penem-3-carboxylate m. p. 164°–67° C.

HPLC: column: μBondaPack $C_{18}$; phase: water/ acetonitrile 60:40. 1-(Cyclohexyloxycarbonyloxy)ethyl (5R,6S)-2-[(2'S,4'R)-2'-carboxyamido-4'-hydroxy-pyrrolidin-1'-yl]methyl-6-[(1R)-1-hydroxyethyl]-penem-3-carboxylate m. p. 176°–77° C.

HPLC: column: μBondaPack $C_{18}$; phase: water/ acetonitrile 50:50. 1-{[(1'S,2'R,5'S)-2'-isopropyl-5'methyl-cyclohexan-1'-yl]oxycarbonyloxy}ethyl (5R,6S)-2[(2'S,4'R)-2'-carboxyamido-4'-hydroxy-pyrrolidin-1'-yl]methyl-6-[(1R)-1-hydroxyethyl]-penem-3-carboxylate m. p. 170°–75° C.

HPLC: column: μBondaPack $C_{18}$; phase: water/ acetonitrile 50:50. Pivaloyloxymethyl (5R,6S)-2-[(2'S,4'R)-2'-carboxyamido-4'-carbamoyloxy-pyrrolidin-1'-yl]methyl-6-[(1R)-1-hydroxyethyl]-penem-3-carboxylate m. p. 173°–75° C.

HPLC: column: μBondaPack $C_{18}$; phase: water/ acetonitrile 50:50. 1-Pivaloyloxyethyl (5R,6S)-2-[(2'S,4'R)-2'-carboxyamido-4'-hydroxy-pyrrolidin-1'-yl]methyl-6-[(1R)-1-hydroxyethyl]-penem-3-carboxylate m. p. 168°–70° C.

HPLC: column: μBondaPack $C_{18}$; phase: water/ acetonitrile 50:50. 1-(Cyclohexylcarbonyloxy)ethyl (5R,6S)-2-[(2'S,4'R)-2'-carboxyamido-4'-hydroxy-pyrrolidin-1'-yl]methyl-6-[(1R)-1-hydroxyethyl]-penem--3-carboxylate m. p. 150°–52° C.

HPLC: column: μBondaPack $C_{18}$; phase: water/ acetonitrile 50:50. (5-tert-butyl-2-oxo-1,3-dioxol-4-yl) methyl (5R,6S)-2-[(2'S,4'R)-2'-carboxyamido-4''-hydroxy-pyrrolidin-1'-yl]methyl-6-[(1R)-1-hydroxyethyl]-penem-3-carboxylate m. p. 172°–74° C.

HPLC: column: μBondaPack $C_{18}$; phase: water/ acetonitrile 50:50. 1-(Isopropylcarbonyloxy)ethyl (5R,6S)-2-[(2'S,4'R)-2'-carboxyamido-4'-hydroxy-pyrrolidin-1'-yl]methyl-6-[(1R)-1-hydroxyethyl]-penem-3-carboxylate m. p. 156–58° C.

HPLC: column: μBondaPack $C_{18}$; phase: water/ acetonitrile 50:50. 1-Pivaloyloxyethyl (5R,6S)-2-[N-(2-acetamido-N-methyl]aminomethyl-6-[(1R)-1-hydroxyethyl]-penem-3-carboxylate m. p. 140°–42° C.

HPLC: column: μBondaPack $C_{18}$; phase: water/ acetonitrile 50:50.

We claim:

1. Penem derivatives of general formula (I), wherein

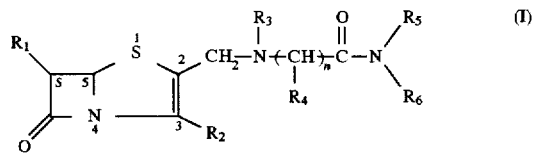

$R_1$ is selected from the group consisting of H, a $C_1$–$C_6$ alkyl, a $C_1$–$C_6$ alkoxy, a $C_3$–$C_7$ cycloalkyl, and an optionally protected $C_1$–$C_6$ hydroxyalkyl;

$R_2$ is selected from the group consisting of a carboxyl group, free or esterified with a group easily activated in vivo, and a carboxylate anion;

$R_3$ is selected from the group consisting of H and a $C_1$–$C_4$ alkyl optionally substituted with a methyl, ethyl, propyl, butyl, pentyl, cyclopentyl, cyclohexyl, phenyl, benzyl, OH, $C_1$–$C_6$ alkoxy, carboxyamidic, carboxyester, or carbamoyloxy group;

$R_4$ is selected from the group consisting of H, a $C_1$–$C_6$ alkyl, a $C_1$–$C_6$ hydroxyalkyl, a $C_1$–$C_6$ mercaptoalkyl, a $C_1$–$C_6$ aminoalkyl, a $C_1$–$C_6$ alkyl substituted by a quaternary ammonium group, a $C_1$–$C_6$ carboxyalkyl, a $C_3$–$C_7$ cycloalkyl, a $C_6$–$C_{10}$ aryl, a $C_6$–$C_{10}$ aryl $C_1$–$C_6$alkyl all these groups optionally substituted with a methyl, ethyl, propyl, butyl, pentyl, cyclopentyl, cyclohexyl, phenyl, benzyl, OH, $C_1$–$C_6$ alkoxy, carboxyamidic, carboxyester, or carbamoyloxy group) and the side chain of a natural alpha amino acid or $R_3$ and $R_4$ linked together form a heterocyclic ring selected from the group consisting of 1-aziridene, 1-pyrrolidine, 1-azetidine, 1-piperidine, 4-morpholine, 1-piperazine, and 4-methyl-1-piperazine, optionally substituted with a methyl, ethyl, propyl, butyl, pentyl, cyclopentyl, cyclohexyl, phenyl, benzyl, OH, $C_1$–$C_6$ alkoxy, carboxyamidic, carboxyester, or carbamoyloxy group; and $R_5$ and $R_6$ independently from one another are selected from the group consisting of H, a $C_1$–$C_6$ alkyl, a $C_1$–$C_6$ hydroxyalkyl, a $C_1$–$C_6$ mercaptoalkyl, a $C_1$–$C_6$ aminoalkyl, a $C_2$–$C_6$ alkenyl, a $C_3$–$C_7$ cycloalkyl, a $C_6$–$C_{10}$ aryl, a $C_6$–$C_{10}$ aryl $C_1$–$C_6$ alkyl, $C_1$–$C_6$ alkyl $C_6$–$C_{10}$ aryl, and a $C_1$–$C_6$ alkyl carboxyamide wherein the alkyl group can be linear or branched (all these groups optionally substituted with a methyl, ethyl, propyl, butyl, pentyl, cyclopentyl, cyclohexyl, phenyl, benzyl, OH, $C_1$–$C_6$ alkoxy, carboxyamidic, carboxyester, or carbamoyloxy group)

or $R_5$ and $R_6$ taken together form a heterocyclic ring selected from the group consisting of 1-aziridene, 1-pyrrolidine, 1-azetidine, 1-piperidine, 4-morpholine, 1-piperazine, 4-methyl-1-piperazine, optionally substituted with a methyl, ethyl, propyl, butyl, pentyl, cyclopentyl, cyclohexyl, phenyl, benzyl, OH, $C_1$–$C_6$ alkoxy, carboxyamidic, carboxyester, or carbamoyloxy group;

n is an intiger from 1 to 3;

and pharmaceutically acceptable salts thereof.

2. Penem derivatives according to claim 1 having a configuration 5R,6S.

3. Penem derivatives according to claim 2 wherein $R_1$ is an alpha-hydroxyethyl group wherein the alpha-C atom of the ethyl group has configuration R.

4. Penem derivatives according to claim 3 wherein $R_2$ is selected from the group consisting of a carboxylate anion and a carboxylic group free or esterified with a compound of general formula (a) or (b)

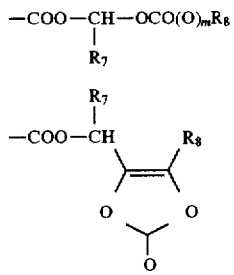

wherein $R_7$ and $R_8$ are selected from the group consisting of H, a $C_1$–$C_6$ alkyl, a $C_2$–$C_6$ alkenyl, a $C_3$–$C_8$ cycloalkyl or cycloalkenyl, a $C_6$–$C_{10}$ aryl and $C_1$–$C_6$ alkyl $C_6$–$C_{10}$ aryl, and m is 0 or 1; and $R_3$ is selected from the group consisting of methyl and ethyl, both optionally substituted with a methyl, ethyl, propyl, butyl, pentyl, cyclopentyl, cyclohexyl, phenyl, benzyl, OH, $C_1$–$C_6$ alkoxy, carboxyamidic, carboxyester, or carbamoyloxy group.

5. Penem derivatives according to claim 4 selected from the group consisting of (5R,6S)-2-(N-(2-acetamido)-N-methyl)-aminomethyl)-6-[(1R)-1-hydroxyethyl]-penem-3-carboxylic acid (5R,6S)-2-((N-prolinamido)-methyl)-6-[(1R)-1-hydroxyethyl]-penem-3-carboxylic acid (5R, 6S) -2- (N-methyl-phenylalaninamido) -methyl-6-[(1R) -1-hydroxyethyl]-penem-3-carboxylic acid (5R,6S)-2-(3'-carboxyamido-piperidin-1'-yl)-methyl-6-[(1R)-1-hydroxyethyl]-penem-3-carboxylic acid (5R,6S)-2-(N,N-diacetamido)-aminomethyl-6-[(1R)-1-hydroxy-ethyl]-penem-3-carboxylic acid (5R,6S)-2-(N-methyl-N-(3'-propionamido)-aminomethyl-6-[(1R)-1-hydroxyethyl]penem-3-carboxylic acid (5R,6S)-2-(N-methyl-N-(4'-methyl-1'piperazin) amidocarboxy-methyl-aminomethyl-6-[(1R)-1-hydroxyethyl]-penem-3-carboxylic acid (5R,6S)-2-(N-ethyl-N-(2'-acetamido)-aminomethyl-$^6$-[(1R)-1-hydroxyethyl]-penem-3-carboxylic acid (5R,6S)-2-(N-methyl-N-((N',N'-dimethyl)acetamido)-amino-methyl-6-[(1R)-1-hydroxyethyl]-penem-3-carboxylic acid (5R,6S)-2-(2'-carboxyamido-piperidin-1'-yl)-methyl-6-[(1R)-1-hydroxyethyl]-penem-3-carboxylic acid (5R, 6S) -2- (4'-carboxyamido-piperidin-1'-yl) -methyl-6-[(1R) -1-hydroxyethyl]-penem-3-carboxylic acid (5'-Methyl-2'-oxo-1',3'-dioxolen-4'-yl)methyl(5R,6S)-2-(N-prolinamido)methyl-6-[(1R)-1-hydroxyethyl]-penem-3-carboxylate Acetoxymethyl (5R,6S)-2-(N-methyl-N-(2-acetamido))-amino-methyl-6-[(1R)-1-hydroxyethyl]-penem-3-carboxylate (5R,6S)-2-(2'-carboxyamido-aziridin-1'-yl)-methyl-$^6$-[(1R)-1-hydroxyethyl]-penem-3-carboxylic acid (5R, 6S) -2- (N-(D-prolinamido)) -methyl-6-[(1R) -1-hydroxy-ethyl]-penem-3-carboxylic acid (5R,6S)-2-[N-methyl-(N'-glycinamido)-glycyl]-aminomethyl-$^6$-[(1R)-1-hydroxyethyl]-penem-3-carboxylic acid Sodium (5R,6S)-2-(N-methyl-N-(2-acetamido)-aminomethyl-$^6$-[(1R)-1-hydroxyethyl]-penem-3-carboxylate Acetoxymethyl (5R,6S)-2-(N-prolinamido)methyl-6-[(1R)-1-hydroxyethyl]-penem-3-carboxylate (5'-methyl-2'-oxo-1',3'-dioxolen-4'-yl)methyl (5R,6s)-2-(N-(2-acetamido)-N-methyl]-aminomethyl-6-[(1R)-1-hydroxyethyl]-penem-3-carboxylate (5R,6S)-2-[(2'S,4'R)-2'-carboxyamido-4'-hydroxy-pyrrolidin-1'-yl]-methyl-6-[(1R)-1-hydroxyethyl]-penem-3-carboxylic acid (5R,6S)-2-(N-(2S)-2-propionamido-N-methyl]-aminomethyl-6-[(1R)-1-hydroxyethyl]-penem-3-carboxylic acid Pivaloyloxymethyl (5R,6S)-2-(N-prolinamido)methyl-6-[(1R)-1-hydroxyethyl]-penem-3-carboxylate Pivaloyloxymethyl (5R,6S)-2-(N-acetamido)-N-methyl-6-[(1R)-1-hydroxyethyl]-penem-3-pivaloyloxymethyl carboxylate (5R,6S)-2-[N-(2'R)-2'-propionamido-N-methyl]aminomethyl-6-[(1R)-1-hydroxyethyl]-penem-3-carboxylic acid (5R,6S)-2-[(2'R,4'R)-2'-carboxyamido-4'-hydroxy-pyrrolidin-1'-yl]methyl-6-[(1R)-1-hydroxyethyl]-penem-3-carboxylic acid (5R,6S)-2-[(2'S,4'S)-2'-carboxyamido-4'-hydroxy-pyrrolidin-1'-yl]methyl-6-[(1R)-1-hydroxyethyl]-penem-3-carboxylic acid (5R,6S)-2-[(2'R,4'S)-2'-carboxyamido-4'-hydroxy-pyrrolidin-1'-yl]methyl-6-[(1R)-1-hydroxyethyl]-penem-3-carboxylic acid (5R,6S)-2-[(2'S,4'R)-2'-carboxyamido-4'-carbamoyloxy-pyrrolidin-1'-yl]methyl-6-[(1R)-1-hydroxyethyl]-penem-3-carboxylic acid Pivaloyloxymethyl (5R,6S)-2-[N-(D-prolinamido)]methyl-6-[(1R)-1-hydroxyethyl]-penem-3-carboxylate (5-methyl-2-oxo-1,3-dioxol-4-yl) methyl(5R,6S)-2-[N-(D-prolinamido)]methyl-6-[(1R)-1-hydroxyethyl]-penem-3-carboxylate Acetoxymethyl (5R,6S)-2-[N-(2'S)-2'-propionamido-N-methyl]aminomethyl-6-[(1R)-1-hydroxyethyl]-penem-3-carboxylate Pivaloyloxymethyl (5R,6s)-2-[N-(2'S)-2'-propionamido-N-methyl]-aminomethyl-6-[(1R)-1-hydroxyethyl]-penem-3-carboxylate (5-methyl-2-oxo-1,3-dioxol-4-yl)methyl(5R,6S)-2-[N-(2'S)-2'-propionamido-N-methyl]aminomethyl-6-[(1R) -1-hydroxyethyl]-penem -3-carboxylate Pivaloyloxymethyl (5R,6S)-2-[(2'S,4'R)-2'-carboxyamido-4'-hydroxy-pyrrolidin-1'-yl]methyl-6-[(1R)-1-hydroxyethyl]-penem-3-carboxylate (5-methyl-2-oxo-1,3-dioxol-4-yl)methyl (5R,6S)-2-[(2'S,4'R)-2'-carboxyamido-4'-hydroxy-pyrrolidin-1'-yl]methyl-6-[('R)-'-hydroxyethyl]-penem-3-carboxylate Cyclohexylcarbonyloxymethyl (5R,6S)-2-[(2'S,4'R)-2'-carboxyamido-4'-hydroxy-pyrrolidin-1'-yl]methyl-6-[(1R) -1-hydroxyethyl]-penem-3-carboxylate 1-(Cyclohexyloxycarbonyloxy)ethyl (5R,6S)-2-[(2'S,4'R)-2'-carboxyamido-4'-hydroxy-pyrrolidin-1'-yl]methyl-6-[(1R)-1-hydroxyethyl]-penem-3-carboxylate 1-{[(1'S,2'R,5'S)-2'-isopropyl-5'methyl-cyclohexan-1'-yl]oxycarbonyloxy}ethyl (5R,6S)-2[(2'S,4'R)-2'-carboxyamido-4'-hydroxy-pyrrolidin-1'-yl]methyl-6-[(1R)-1-hydroxyethyl]-penem-3-carboxylate Pivaloyloxymethyl (5R,6S)-2-[(2'S,4'R)-2'-carboxyamido-4'-carbamoyloxy-pyrrolidin-1'-yl]methyl-6-[(1R)-1-hydroxyethyl]-penem-3-carboxylate 1-Pivaloyloxyethyl (5R,6S)-2-[(2'S,4'R)-2'-carboxyamido-4'-hydroxy-pyrrolidin-1'-yl]methyl-6-[(1R)-1-hydroxyethyl]-penem-3-carboxylate 1-(Cyclohexylcarbonyloxy)ethyl (5R,6S)-2-[(2'S,4'R)-2'-carboxyamido-4'-hydroxy-pyrrolidin-1'-yl]methyl-6-[(1R)-1-hydroxyethyl]-penem-3-carboxylate (5-tert-butyl-2-oxo-1,3-dioxol-4-yl)methyl (5R,6S)-2-[(2'S,4'R)-2'-carboxyamido-4'-hydroxy-pyrrolidin-1'-yl]methyl-6-[(1R)-1-hydroxyethyl]-penem-3-carboxylate 1-(Isopropylcarbonyloxy)ethyl (5R,6S)-2-[(2'S,4'R)-2'-carboxyamido-4'-hydroxy-pyrrolidin-1'-yl]methyl-6-[(1R)-1-hydroxyethyl]-penem-3-carboxylate 1-Pivaloyloxyethyl (5R,6S)-2-[N-(2-acetamido-N-methyl]aminomethyl-6-[(1R)-1-hydroxyethyl]-penem-3-carboxylate.

6. A pharmaceutical composition comprising comprising a therapeutically effective amount of a compound according to claim 1 in combination with a pharmaceutically acceptable carrier.

7. A pharmaceutical composition according to claim 6 which may be administered orally.

8. A pharmaceutical composition according to claim 6 which may be administered parenterally.

* * * * *

UNITED STATES PATENT AND TRADEMARK OFFICE
CERTIFICATE OF CORRECTION

PATENT NO. : 5,747,483
DATED      : May 5, 1998
INVENTOR(S): Altamura et al

It is certified that error appears in the above-identified patent and that said Letters Patent is hereby corrected as shown below:

On the title page, insert item --[30] Foreign Application Priority Data
September 17, 1992 [IT] Italy....FI 92 A 000181 --

Signed and Sealed this

Fourth Day of April, 2000

Attest:

Attesting Officer

Q. TODD DICKINSON

Director of Patents and Trademarks